US012605273B2

(12) United States Patent
Llopis Manzanera

(10) Patent No.: US 12,605,273 B2
(45) Date of Patent: Apr. 21, 2026

(54) PROLAPSE CORRECTIVE DEVICE

(71) Applicant: Juan Llopis Manzanera, Barcelona (ES)

(72) Inventor: Juan Llopis Manzanera, Barcelona (ES)

( * ) Notice: Subject to any disclaimer, the term of this patent is extended or adjusted under 35 U.S.C. 154(b) by 0 days.

(21) Appl. No.: 18/849,936

(22) PCT Filed: Mar. 21, 2023

(86) PCT No.: PCT/EP2023/057192
§ 371 (c)(1),
(2) Date: Sep. 23, 2024

(87) PCT Pub. No.: WO2023/180308
PCT Pub. Date: Sep. 28, 2023

(65) Prior Publication Data
US 2025/0195262 A1 Jun. 19, 2025

(30) Foreign Application Priority Data
Mar. 24, 2022 (EP) .................................... 22382272

(51) Int. Cl.
*A61F 6/08* (2006.01)
(52) U.S. Cl.
CPC ...................................... *A61F 6/08* (2013.01)
(58) Field of Classification Search
CPC ................ A61F 2230/0023; A61F 6/08; A61F 2220/0008; A61F 2220/0091; A61F 2/005;
(Continued)

(56) References Cited

U.S. PATENT DOCUMENTS

2009/0203959 A1   8/2009   Ziv et al.
2009/0266367 A1   10/2009   Ziv et al.
2021/0282961 A1   9/2021   Maier et al.

FOREIGN PATENT DOCUMENTS

WO     WO-2018140192 A1 *   8/2018   ............. A61F 13/20

OTHER PUBLICATIONS

International Searching Authority, "International Search Report," issued in connection with International Patent Application No. PCT/EP2023/057192, dated Jun. 20, 2023, 4 pages.
(Continued)

*Primary Examiner* — Ophelia A Hawthorne
(74) *Attorney, Agent, or Firm* — Hanley, Flight & Zimmerman, LLC

(57) ABSTRACT

The present invention relates to a prolapse corrective device, made up of a single piece (1) in which can be distinguished a head (2) with an upper ending (21) in the general shape of a dome; two arms (3) opposing and diverging from each other; and a connecting strap (4), the device adopting an expanded position (A) by default in the general shape of a dished isosceles triangle that is elastically deformable when the connecting strap (4) is manually pulled in a direction opposite to the head (2), the device being able to be arranged in a compressed position (B1) that facilitates placing or extracting the device from inside a vagina, the arms (3) responding with a restoring force exerting pressure against the walls of the vagina, the piece (1) being locked under pressure inside the vagina, the device adopting an operative position (B2), when the pulling of the connecting strap (4) stops.

15 Claims, 3 Drawing Sheets

(58) Field of Classification Search
    CPC ........ A61F 6/18; A61F 2/00; A61F 2250/009;
                A61F 2250/001; A61F 2250/0065; A61F
                2250/0071; A61F 6/146; A61B 17/42
    See application file for complete search history.

(56) References Cited

OTHER PUBLICATIONS

International Searching Authority, "Written Opinion," issued in connection with International Patent Application No. PCT/EP2023/057192, dated Jun. 20, 2023, 6 pages.
European Patent Office, "Extended European search report," issued in connection with International Patent Application No. 22382272.7, dated Oct. 19, 2022, 7 pages.

* cited by examiner

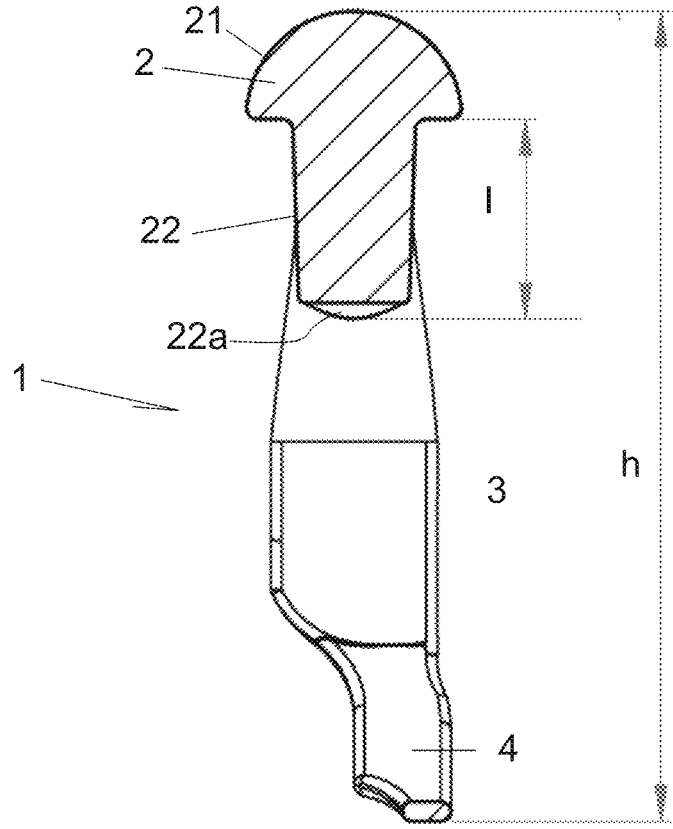
<u>Fig. 3</u>
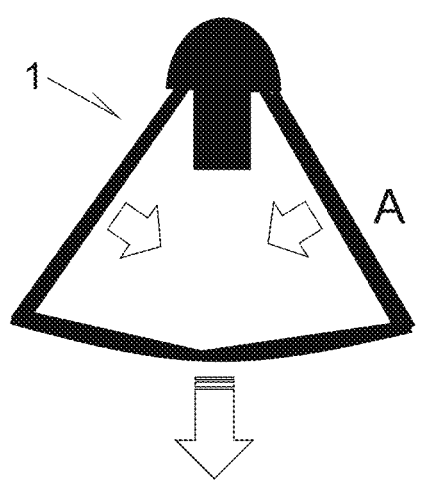
<u>Fig. 4</u>
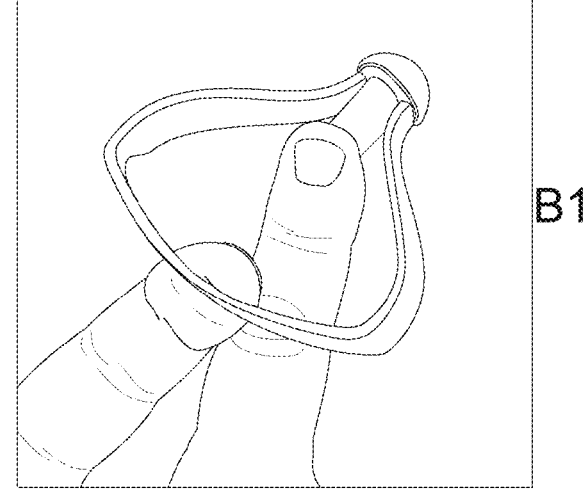
<u>Fig. 5</u>

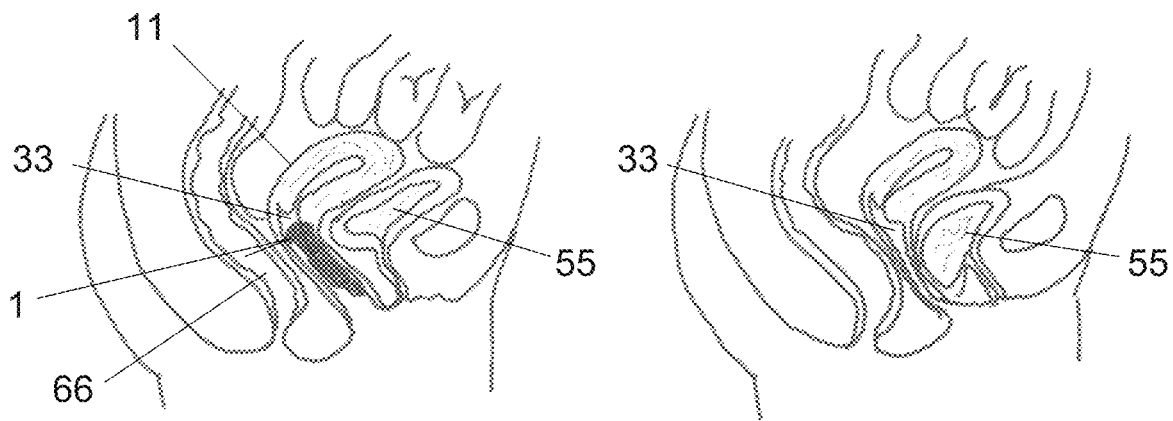
Fig. 7b                                        Fig. 6
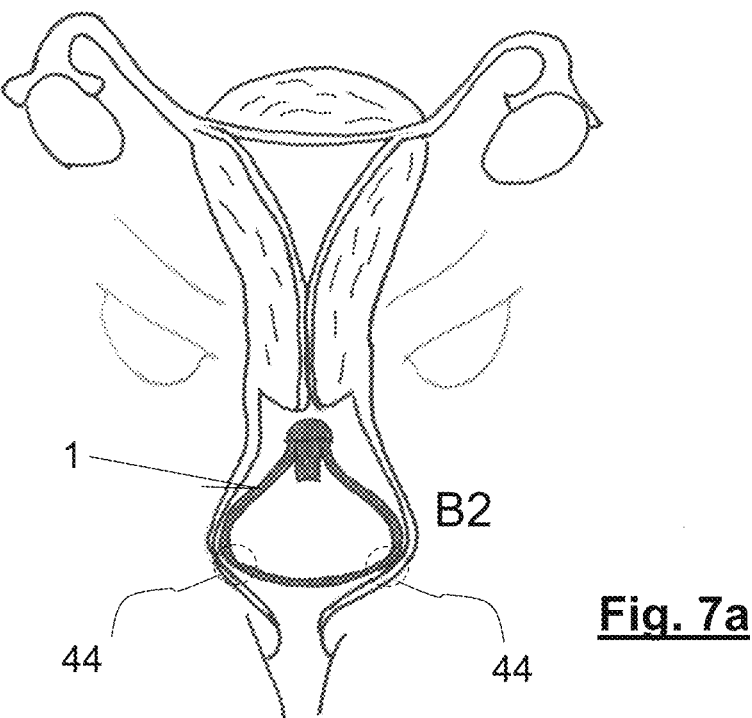
Fig. 7a

PROLAPSE CORRECTIVE DEVICE

CROSS-REFERENCE TO RELATED APPLICATIONS

This patent arises from a U.S. national phase of International Patent Application No. PCT/EP2023/057192, which was filed on Mar. 21, 2023, and which claims priority to European Patent Application No. 22382272.7, which was filed on Mar. 24, 2022. Priority to both International Patent Application No. PCT/EP2023/057192 and to European Patent Application No. 22382272.7 is claimed. International Patent Application No. PCT/EP2023/057192 and European Patent Application No. 22382272.7 are hereby incorporated herein by reference in their entireties.

TECHNICAL FIELD OF THE INVENTION

The invention relates to a prolapse corrective device, especially for reducing the pelvic organ prolapse of a patient, either permanently or temporarily during the performance of a functional study prior to surgical correction.

BACKGROUND OF THE INVENTION

The problem of prolapse or the exit of any pelvic organ (bladder, uterus or rectum) through the vaginal orifice is known in the current state of the art. When a pelvic organ prolapse acquires a significant size, it becomes a problem that requires a solution, often surgical.

In such cases, functional studies are usually performed before planning the intervention, to rule out concealed stress urinary incontinence.

During this type of study, a simulation of the arrangement that the pelvic organs will have after surgical correction is practiced, and the appearance of stress urinary incontinence is forced during the filling of the bladder. If stress urinary incontinence occurs, it is surgically corrected at the same time as the pelvic organ prolapse. The emptying of the bladder in the new placement thereof is also investigated.

The use of pessaries and vaginal packing to solve pelvic organ prolapse is known.

Pessaries are designed for correcting pelvic organ prolapse in a sustained manner in patients awaiting intervention or inoperable patients. They come in different sizes and are changed every six months. During that time they only require regular cleaning. For its temporary use in different patients, sterilisation and the availability of several sets are required. During attempts to demonstrate stress urinary incontinence they may fall out if the size is not properly adjusted.

As far as the packing is concerned, it is nothing more than a rolled gauze, which is then shaped into an arrow. Given the material used, it has two drawbacks: insertion can be uncomfortable and even painful, and it does not maintain its shape inside the vagina.

From patent document EP 3487428 various devices are known to replace or supplement a support of the rear side of the urethra that can help prevent the involuntary flow of urine through the urethra. In a variant, the device has a shape similar to a crossbow, and is equipped with a filiform element, a thread, to tighten the bow which can have a simple arch shape or be configured in the shape of a double S. The device has edges, it requires several portions to be assembled and has a kind of handle or pole to gather the thread and offer the user a loop to pull therefrom.

From patent document U.S. Pat. No. 6,460,542 a device for controlling urinary incontinence is known. The device is made of a single piece that is placed in the vagina, but it is not suitable for correcting prolapse, especially if it is of a high degree, because it does not remain sufficiently locked in the vagina to support the pressure exerted by the offset organs, which causes ejection of the device. In addition, its placement requires portions of the device to be pinched with the fingers to deform it elastically during the placement thereof, the fingers having to be inserted together with the device into the vagina.

It is the main objective of the present invention to provide an alternative to the known devices.

It is also desirable that the device enables the pelvic organ prolapse of a patient to be reduced in a simple, safe and comfortable way for both the patient and the specialist applying it.

EXPLANATION OF THE INVENTION

The proposed prolapse correction device is a device according to claim 1.

The device is made up of a single elastically deformable piece suitable for being located and remaining in the vagina of a patient.

In essence, the device is characterised in that the piece has a head with an upper ending in the general shape of a dome, below which two arms originate and extend opposing and diverging from each other, each arm having a proximal end, for attaching to the head, a central portion and a distal end, the piece further having a connecting strap that extends between and that connects the two arms at the distal ends thereof, the device adopting by default an expanded position in the general shape of a dished isosceles triangle wherein the head is at the vertex, the arms are the sides of the triangle and the connecting strap is the base of the triangle.

It is characteristic of the piece that the arms thereof approach each other, the piece being elastically deformed, when the connecting strap is manually pulled in a direction opposite to the head and pressure by a human finger is simultaneously applied to a lower ending of which said head is provided for said purpose, the device being able to be arranged in a compressed position that facilitates being able to perform a manoeuvre to insert the device inside a vagina or to withdraw the device from inside a vagina.

It is also characteristic of the piece that the arms respond with a restoring force by exerting pressure against the walls of the vagina, the piece being locked under pressure inside the vagina, this is to say snaps into the vagina, the device adopting an operative position, as the piece is to recover the expanded position thereof when the pulling of the connecting strap stops after inserting the same into the vagina.

In the context of the present invention, the term elasticity designates the physical and mechanical property of certain materials of undergoing reversible deformations when they are subjected to the action of external forces and to recover the original shape if these external forces are removed.

In a variant of the invention, the upper ending of the head is in the shape of a hemispherical cap with a radius comprised between 8 and 12 mm.

In a variant of the invention, the lower ending of the head is a protrusion located between the arms, which extends in the opposite direction to the upper ending, in the shadow thereof and without exceeding the gauge of said upper end.

The length dimension of the lower ending is short compared to the height dimension of the piece. As will be explained below, there is an ideal compromise so as not to have to insert the index finger too far into the vagina, to be able to safely push the piece and save on material costs and to dispense with elements or portions that can be uncomfortable when the piece is placed inside the vagina.

In a variant of interest, the lower ending extends a length, below the upper ending, of between 15 to 20 mm.

The lower ending may have, at the distal end thereof, a concave surface intended for a human finger to be supported.

The lower ending may be of a generally frustoconical shape, narrowing towards the distal end thereof.

In a variant of the invention, the proximal ends of the arms originate below the upper ending of the head and extend tangentially thereto; the central portions follow a slightly S-shaped profile that equips the arms with a slight outward arch; and the distal ends are rounded to link, without interruption, with the connecting strap, also slightly arched towards the outside of the piece.

Preferably, the assembly of the head and the arms of the piece is symmetrical with respect to a first and a second plane of symmetry orthogonal to each other; while the connecting strap is not symmetrical with respect to the first plane of symmetry, being slightly offset to one side of said first plane of symmetry, all this to facilitate the handling of the device during the manoeuvres of insertion and extraction of the same from a vagina, as explained in more detail below.

In particular and in a variant, the connecting strap also narrows along a central portion thereof.

The narrowness of the connecting strap can be implemented in the form of an indentation formed on the lateral edge thereof which is oriented towards the inside of the piece.

Preferably, the outer surface of the arms is a curved surface, concave with respect to the free space defined between said arms to minimise discomfort while they are supported on a soft tissue inside the vagina.

In a variant of the invention, in each transition area between the arms and the connecting strap there is a reduction in material in the piece, with the purpose of having this transition area deploying a hinge effect that facilitates the deformation of the piece. This also contributes to facilitating the handling of the device during the manoeuvres of insertion and extraction of the same from a vagina.

Preferably, the height dimension of the generally dished triangle shape that the piece has is comprised between 60 and 70 mm, more preferably being between 64 and 66 mm; and the width dimension of the generally dished triangle shape that the piece has is comprised between 80 and 90 mm, more preferably being between 84.5 and 86.5 mm.

The piece defines two lower support areas, in a correctly placed position in a vagina. The practical extension of these support areas varies according to each patient and depending on the degree of compression that the piece adopts when it is placed, but it usually covers between 7 to 10% of the extension of the base of the dished triangle shape, to each side thereof. Preferably, the height of the piece from these lower support areas to the tip of the head is between 63 to 67 mm.

The absolute values of the dimensions indicated have a margin of ±5%.

BRIEF DESCRIPTION OF THE DRAWINGS

FIG. 3 is a cross sectional view according to the section plane AA indicated in FIG. 1;

FIGS. 4 and 5 are respective schematic views, which intend to show a way of handling the device;

FIG. 6 is a schematic view of a typical cystocele condition; and

FIGS. 7a and 7b, are respective schematic views showing the device in an operative position, inside a vagina to correct the condition of FIG. 6.

DETAILED DESCRIPTION OF AN EMBODIMENT

Figures 1, 2:
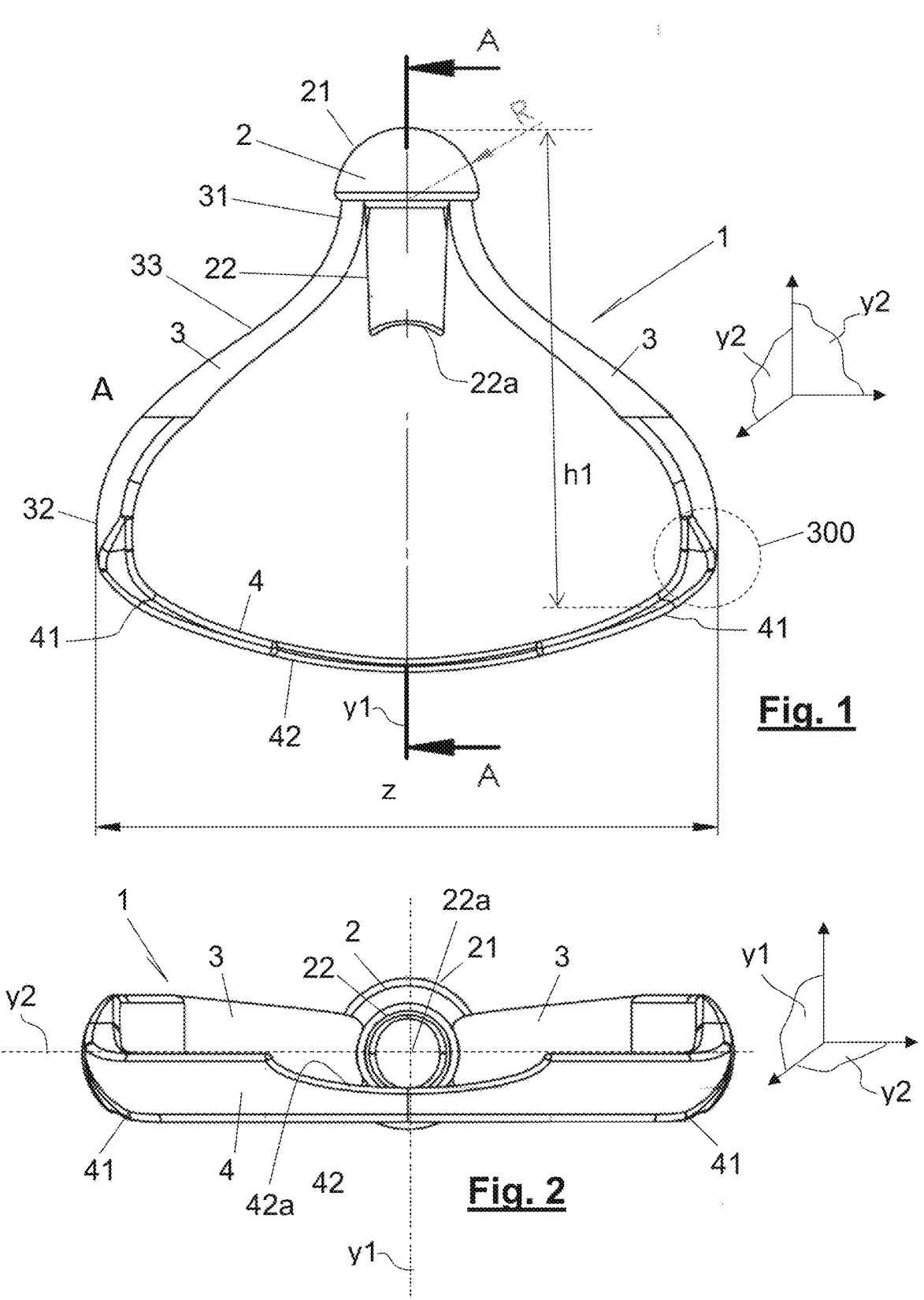
FIGS. 1 to 2 are respective front and lower elevation views of a device according to the invention.

A device according to the invention is exemplified in FIGS. 1 to 3.

The device is made up of a single elastically deformable piece 1. Biocompatible materials suitable for producing the piece 1, the design of which is such that it can be produced following conventional injection moulding techniques, are synthetic resins, such as silicones, or various plastic materials, such as polyolefins, urethanes, ABS or thermoplastic elastomers or combinations of materials that offer the necessary restoring force for the piece to fit snugly inside a vagina, all as explained in greater detail below.

With reference to FIG. 1, the piece 1 has the general shape of a dished isosceles triangle at the vertex of which there is a head 2 with an upper ending 21 in the general shape of a dome, in the example in the shape of a hemispherical cap of radius R, below which two equal and opposite arms 3 originate and extend, diverging from each other, which define the sides of the general shape of the aforementioned dished triangle.

Each arm 3 has a proximal end 31, for attaching to the head 2; a central portion 33; and a distal end 32.

The proximal ends 31 originate and extend tangentially with respect to the upper ending 21 of the head 2; the central portions 33 follow a slightly S-shaped profile that equips the arms 3 with a slight outward arch; and the distal ends 32 are rounded to link, without interruption, with a connecting strap 4 that connects to the arms 3 by the distal ends 32 thereof, this connecting strap 4 defining the base in the general shape of a dished triangle.

This connecting strap 4 is also slightly dished towards the outside of the piece 1 and two opposite ends 41 can be distinguished therein, whereby the connecting strap 4 is attached to the distal ends 32 of the arms 3, and a central pulling portion 42.

It should be noted that the piece 1 has a smooth surface on the outside and, as already mentioned, the attachment between the arms 3 and the connecting strap 4 is uninterrupted, i.e., the outside surface of the piece 1 in each transition area 300 between the arms 3 and the connecting strap 4 (which would be the vertexes of the base of the general triangular shape of the piece) is all rounded, since they will be anchoring points of the piece 1 inside a vagina. Likewise, the outer surface of the arms 3 is a curved surface, concave with respect to the free space defined between said arms 3 so that the support thereof on the inner walls of the vagina, which is a soft tissue, is not uncomfortable.

FIG. 1 shows the piece 1 in a position in which the head 2 points upwards; and the connecting strap 4 is below. This orientation is similar to the one that the piece 1 will adopt during use thereof.

The piece 1 has certain symmetries. Specifically, in the exemplary variant, the head 2 and the arms 3 of the piece 1 have symmetry with respect to two orthogonal planes, which intersect coinciding with an imaginary straight line, coinciding with the bisector of the angle defined by the arms 3 and coaxial with the axis of the hemispherical cap of the upper ending 21 of the head 2.

FIG. 1 shows, among other aspects, the symmetry that the head 2 and the arms 3 have with respect to a first plane of symmetry y1, orthogonal to the plane of the paper in FIG. 1, and wherein the aforementioned imaginary straight line is inscribed.

FIG. 2 is a lower view of the piece 1 that shows, among other aspects, the symmetry that the head 2 and the arms 3 also have with respect to a second plane of symmetry y2, orthogonal to the first plane of symmetry y1 and to the plane of the paper in FIG. 2, wherein the imaginary straight line is also inscribed.

FIG. 3 is a cross sectional view of the piece 1 according to the section plane AA indicated in FIG. 1, which coincides with the first plane of symmetry y1.

The shape represented in FIGS. 1 and 2 is the shape that the piece 1 naturally adopts. This position is referred to as expanded position A.

In order to place the piece 1 in a vagina and deploy the purpose thereof, the piece is specially configured so that the arms 3 thereof can come closer together, the piece 1 being elastically deformed until it adopts a compressed position B1. In this compressed position B1, the piece is inserted into the vagina by the head 2 thereof, the hemispherical cap shape of the upper ending 21 thereof facilitating this insertion operation.

This deformation can be done manually, without auxiliary instruments. In addition, this operation can be performed without having to externally rest the fingers on the arms 3 to manually clamp the piece 1 and having to insert the fingers into the vagina.

For this, the head 2 has a lower ending 22 especially suitable and sized for a finger to be supported, such as an index finger and press on the same while the connecting strap 4 is pulled in the opposite direction, as if drawing a bow, using the fingers of another hand for that purpose.

FIGS. 4 and 5 are respective vignettes that intend to illustrate this way of proceeding, to move the piece 1 from the expanded position A of FIG. 4 until the piece 1 adopts the compressed position B1 in FIG. 5.

With regard to the aforementioned lower ending 22 of the head 2, in the example it does not protrude from the gauge of the upper ending 21, i.e., it is hidden behind the hemispherical cap and between the arms 3. In the variant of the drawings, this lower ending 22 has, at the distal end thereof, a concave surface 22a intended precisely for an index finger to be supported, the lower ending 22 being generally frustoconical in shape, narrowing in the direction of the distal end thereof.

To make the manoeuvre for placing the device even easier, the connecting strap 4 is specially designed to leave more space for the index finger that pushes the head 2 of the piece 1 from below. As can be seen in FIGS. 2 and 3, the connecting strap 4 is of reduced width compared to the arms 3; it is slightly offset to one side of the second plane of symmetry y2; and it has a slight indentation 42a in the central pulling portion 42 thereof, on the edge of the latter oriented towards the inside of the piece 1. This accumulation of features facilitates the deformation of the piece 1 by concentrating less material in the attachment areas between the connecting strap 4 and the arms 3, these areas performing a kind of hinge or joint effect, while emptying this portion of the piece 1 to leave more passage space for the index finger to be supported under the head 2 of the piece 1.

Once the piece 1 is correctly located inside the vagina, the fingers can be removed from the piece to allow it to tend to recover the natural position thereof, the arms 3 responding with a restoring force by exerting pressure against the inner walls of the vagina, the piece 1 remaining locked under pressure inside the vagina and the device adopting an operative position B2 (see FIG. 7a).

FIG. 6 is a schematic view intended to show a typical cystocele condition. A cystocele is a condition in which the supportive tissues around the bladder 55 and the vaginal wall weaken and stretch, allowing the bladder 55 and vaginal wall to fall into the vaginal canal 33.

FIGS. 7a and 7b show the piece 1 in the operative position B2 thereof to correct this condition. It can be seen how the head 2 of the device rests on the uterine neck or cervix. The lateral arms 3 are supported on the lateral vaginal walls on the external side thereof; on the front vaginal wall, on which the urinary bladder 55 rests, on the upper side thereof and on the rear vaginal wall, on which the rectum 66 is supported, on the lower side thereof, all offering support to maintain the uterus in position 11 and offering support for the rectum and the bladder, the uterine prolapse, rectocele and cystocele being corrected.

It is conceivable to have a set of pieces 1 of different sizes, according to the morphology of each patient or the shape of the vagina. However, the particular configuration of the piece 1 makes it possible to find proportions designed or suitable so that the piece 1 is universal and several sizes are not required, as opposed to traditional pessaries that have up to more than 10 sizes.

Thus, for example, the height dimension h of the piece 1 (see FIG. 3) is preferably comprised between 60 and 70 mm, a height h1=65±2 mm being of special interest (see FIG. 1); in combination with a preferred width dimension z of the piece 1 (see FIG. 1) between 80 and 90 mm, a width of z=85.6 mm being of special interest.

The height dimension h1 is that which goes from the level of the tip of the head 2 to the most distant level of the lower support area 44 of the piece 1 when it is placed in a vagina, which corresponds to the end transition area between the arms and the connecting strap (see also FIG. 7a). This support area approximately covers between 7 to 10% of the width of the base of the triangle shape of the piece 1, on each side of said base.

It can be observed that the minimum width dimension is greater than the maximum height dimension, which gives the piece 1 in these preferred cases a flattened shape, i.e., it is wider than it is high.

For the head 2, a hemispherical cap shape is selected for the upper ending 21 thereof with a radius R between 9 and 11 mm, a radius R=10 mm being of special interest.

For the lower ending 22 of the head 2, there is an ideal compromise so as not to have to insert the index finger too far into the vagina, to be able to safely push the piece 1 and save on material costs, as well as to dispense with elements or portions that can be uncomfortable when the piece 1 is placed. In the variant that exemplifies the invention, a length l is conceived for the lower ending 22 (see FIG. 3) between 20 and 17 mm, a length l=18.5 mm being of special interest.

The invention claimed is:

1. A prolapse corrective device comprising:
   a single elastically deformable piece configured to be located and to remain in a vagina of a patient,
     the single elastically deformable piece has a head with an upper ending in a dome shape, below which two arms originate and extend, opposing and diverging from each other, each arm having a proximal end for attaching to the head, a central portion and a distal end, the single elastically deformable piece further having a connecting strap that extends between and that connects the two arms at the distal ends thereof, the device adopting an expanded position by default in a shape of a dished isosceles triangle wherein the head is at a vertex of the triangle, the arms are at sides of the triangle and the connecting strap is a base of the triangle, wherein the arms of the single elastically deformable piece are approachable to each other, the single elastically deformable piece being elastically deformed, when the connecting strap is manually pulled in a direction opposite to the head and a pressure by a human finger is simultaneously applied on a lower ending of said head, the device being able to be arranged in a compressed position that facilitates insertion of the device inside the vagina or removal of the device from inside the vagina, the arms responding with a corresponding restoring force, enough to exert pressure against walls of the vagina as the single elastically deformable piece tends to recover the expanded position thereof when the pulling of the connecting strap stops after inserting the single elastically deformable piece into the vagina, so that the device adopts an operative position.

2. The device according to claim 1, wherein the lower ending of the head is a protrusion located between the arms, the lower ending extends in a direction opposite to the upper ending, without exceeding a gauge of the upper ending.

3. The device according to claim 2, wherein the lower ending extends a length, below the upper ending, between 15 to 20 mm.

4. The device according to claim 2, wherein the lower ending has, at the distal end thereof, a concave surface intended for a human finger to be supported.

5. The device according to claim 2, wherein the lower ending is generally frustoconical in shape, narrowing towards the distal end thereof.

6. The device according to claim 1, wherein:
a height dimension of the dished isosceles triangle is between 60 and 70 mm, and
a width dimension of the dished isosceles triangle is between 80 and 90 mm.

7. The device according to claim 6, wherein the height of the dished triangle shape from a lower support area, which corresponds to an end transition area between the arms and the connecting strap, to a tip of the head is between 63 to 67 mm, the lower support area covering between 7 to 10% of the width of the base of the triangle shape of the single elastically deformable piece.

8. The device according to claim 6, wherein the width dimension of the dished isosceles triangle is between 84.5 and 86.5 mm.

9. The device according to claim 1, wherein the connecting strap narrows along a central pulling portion thereof.

10. The device according to claim 9, wherein the narrowness of the connecting strap is an indentation on the lateral edge thereof.

11. The device according to claim 1, wherein the upper ending of the head is in the shape of a hemispherical cap with a radius comprised between 8 and 12 mm.

12. The device according to claim 1, wherein the proximal ends of the arms originate below the upper ending of the head and extend tangentially thereto; central portions of the arms follow a slightly S-shaped profile that equips the arms with a slight outward arch towards an outside of the single elastically deformable piece with a concavity directed towards an inside of the single elastically deformable piece; and the distal ends are rounded to link, without interruption, with the connecting strap.

13. The device according to claim 1, wherein the head and the arms are symmetrical with respect to a first and a second plane of symmetry which are orthogonal to each other; and the connecting strap is not symmetrical with respect to the first plane of symmetry, being slightly offset to one side of said first plane of symmetry.

14. The device according to claim 1, wherein outer surfaces of the arms are curved and concave with respect to a free space defined between said arms.

15. The device according to claim 1, wherein in each transition area between the arms and the connecting strap there is a reduction in material in the single elastically deformable piece, each of the transition areas providing a hinge effect that facilitates deformation of the single elastically deformable piece.

* * * * *